US00PP22003P2

(12) United States Plant Patent
Sidhu

(10) Patent No.: US PP22,003 P2
(45) Date of Patent: Jul. 5, 2011

(54) *THUJA* PLANT NAMED 'THUSID 1'

(50) Latin Name: *Thuja occidentalis*
Varietal Denomination: Thusid 1

(76) Inventor: Gurjit Sidhu, Mission (CA)

( * ) Notice: Subject to any disclaimer, the term of this patent is extended or adjusted under 35 U.S.C. 154(b) by 0 days.

(21) Appl. No.: 12/800,303

(22) Filed: May 12, 2010

(51) Int. Cl.
*A01H 5/00* (2006.01)

(52) U.S. Cl. ..... Plt./213

(58) Field of Classification Search ..... Plt./213
See application file for complete search history.

*Primary Examiner* — Annette Para

(74) *Attorney, Agent, or Firm* — Penny J. Aguirre

(57) ABSTRACT

A new cultivar of *Thuja occidentalis* named 'Thusidl' characterized by its semi-dwarf, narrow columnar habit, fine-textured, dark green foliage and contrasting new growth that is bright yellow in color.

2 Drawing Sheets

Botanical classification: *Thuja occidentalis.*
Varietal denomination: 'Thusid 1'.

BACKGROUND OF THE INVENTION

The present invention relates to a new and distinct cultivar of *Thuja occidentalis* and will be referred to hereafter by its cultivar name, 'Thusid 1'. 'Thusid 1' represents a new western red cedar, an evergreen tree grown for landscape use.

The inventor discovered this new *Thuja* (un-patented) as a naturally-occurring branch mutation of *Thuja occidentalis* 'Smargd' (not patented) in Spring of 2006 in a block of 5 containers in one of the production sites in Mission, B.C., Canada.

Asexual reproduction of the new cultivar was first accomplished by stem cuttings in Mission, B.C., Canada in winter of 2006 by the inventor. Further generations of cuttings were taken in following years and trials have determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Thusid1', as unique from all other selections and forms of *Thuja occidentalis* known to the inventor.

1. 'Thusidl' exhibits deep green foliage with bright yellow new growth.
2. 'Thusidl' exhibits fine textured foliage.
3. 'Thusidl' exhibits a narrow columnar growth habit.

'Thusid1' differs from its parent plant, 'Smargd', in having new growth that is bright yellow in color. 'Thusid1' can be compared to other semi-dwarf cultivars of *Thuja occidentalis*. 'Sherwood Frost' (not patented) is similar to 'Thusid1' in general habit but differs in being taller in height and wider in spread. 'Holmstrup' (not patented) is similar in height and width but differs in having gray-green foliage.

BRIEF DESCRIPTION OF THE DRAWING

The plant and plant parts depicted in the accompanied photographs illustrate the characteristics of 'Thusid1' (left) in comparison to 'Smargd' (right). The photographs were taken of two year-old plants grown outdoors in one-gallon containers in Mission, B.C., Canada.

DETAILED BOTANICAL DESCRIPTION

Figure 1:
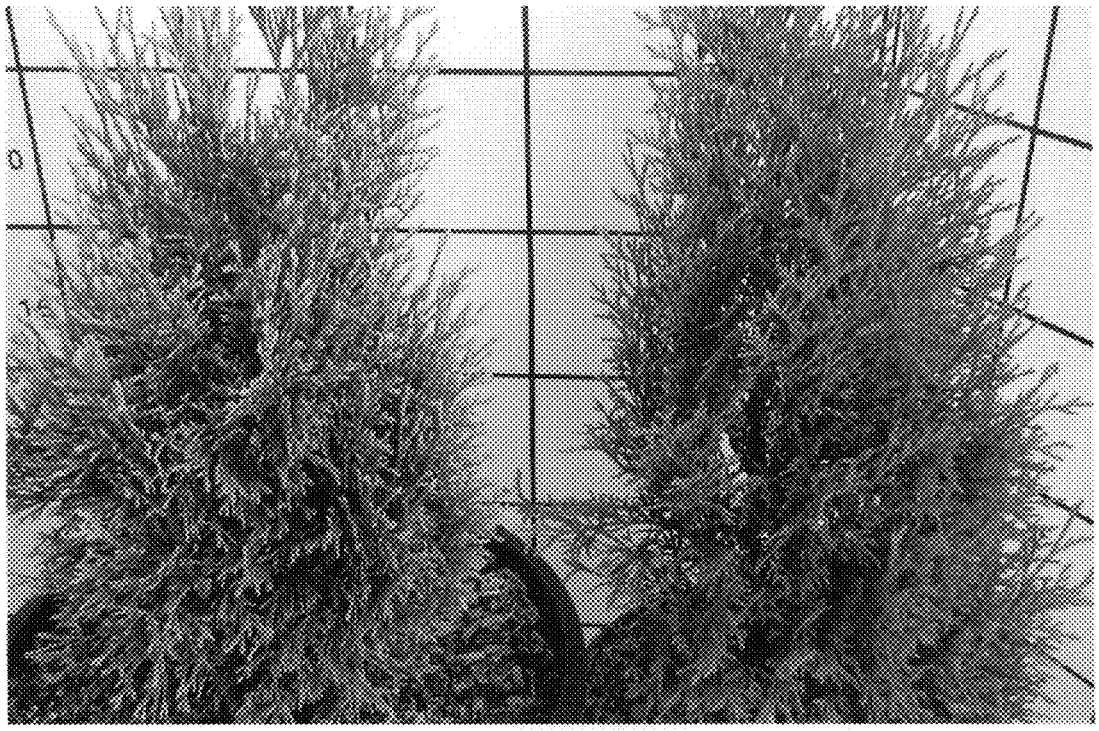
FIG. 1 provides an overall view of the habit and foliage texture of the two plants.
Figure 2:
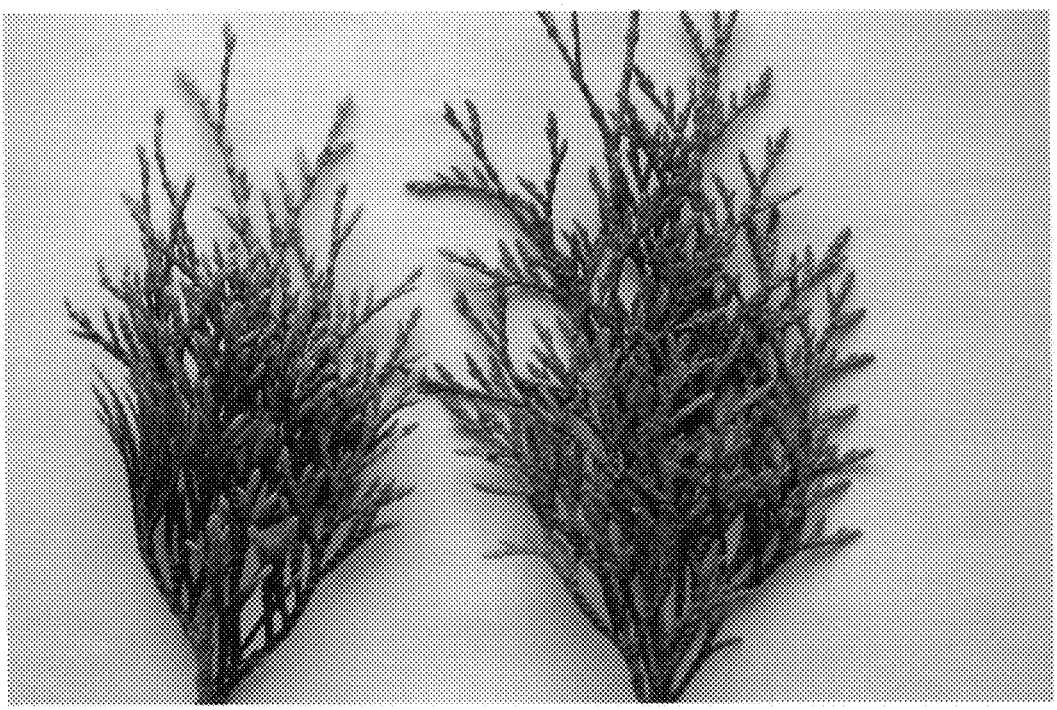
FIG. 2 provides a close-up view of the foliage of the two plants. The colors in the photographs are as close as possible with the photographic and printing technology utilized. The color values cited in the detailed botanical description accurately describe the colors of the new *Thuja.*

The following is a detailed description of the new cultivar as taken from two year-old plants from stem cuttings as grown in one-gallon containers in Mission, B.C., Canada. The phenotype of the new cultivar may vary with variations in environmental, climatic, and cultural conditions, as it has not been tested under all possible environmental conditions. The color determination is in accordance with the 2007 R.H.S. Colour Chart of The Royal Horticultural Society, London, England, except where general color terms of ordinary dictionary significance are used.

General description:

*Plant type.*—Coniferous, evergreen, tree for landscape use.

*Growth habit.*—Semi-dwarf, narrowly pyramidal with fine foliage.

*Height and spread.*—An average of 21 cm in height and 13 cm in width as grown in a one-gallon container, reaching an average of 4.5 m in height and 1 m in width at maturity.

*Cone development.*—Neither male nor female cones have been observed.

*Cold hardiness.*—U.S.D.A. Zones 2 to 7.

*Diseases and pests.*—No susceptibility or resistance to diseases or pests known to affect *Thuja* has been observed.

*Root description.*—Fibrous.

*Growth rate.*—Moderate.

*Propagation.*—Semi-hardwood cuttings.

Stem description:

*Shape.*—Oval.

*Stem size.*—Main branch: average of 1 cm in diameter and 17 cm in length; lateral branches: average of 3 mm in diameter and 10 cm in length.

*Stem surface.*—Young branches are glabrous and knobby with scales.

*Branching.*—Main stem arises from base with numerous secondary branches, number of lateral branches an average of 34 per main stem 17 cm in length.

*Branch arrangement.*—Alternate (closely on twigs).

*Branch aspect.*—Main stems upright, lateral stems held at about an average of 45° angle from the main stem with flat sprays that spread outwards.

*Internode length.*—Range from 3 cm at the base to 1 cm at the tip.

*Stem color.*—New growth on sprays (twigs) are N199C with scales N167D, young branches 166B with scales 166A, branches mature to 177A.

Foliage description:

*Leaf arrangement.*—Numerous leaves arranged on planar branchlets (closely alternate or opposite), scale-like decussate.

*Leaf shape.*—Facial pair keeled, flat pair flattened and oblong.

*Leaf division.*—Simple.

*Leaf base.*—Cuneate.

*Leaf apex.*—Apiculate.

*Leaf venation.*—Not visible.

*Leaf margins.*—Entire.

*Leaf surface.*—Upper and lower; glabrous, smooth, glossy.

*Leaf color.*—Mature upper surface: blend of 143A to 137A; mature lower surface: 137B; new growth upper and lower surface; 11A to 11C in color.

*Leaf fragrance.*—Cedar scented when crushed.

*Leaf size.*—A average of 2 mm in length and 1 mm in width.

*Leaf quantity.*—About 15 leaves per cm in lateral branches.

Cone description: No cones have been observed on the plants trialed for data collection.

It is claimed:

1. A new and distinct cultivar of *Thuja* plant named 'Thusid1' as herein illustrated and described.

* * * * *